United States Patent [19]
Perry

[11] Patent Number: 5,861,265
[45] Date of Patent: *Jan. 19, 1999

[54] BINDING ASSAY METHOD USING A SIGNAL PREVENTING REAGENT

[75] Inventor: Martin John Perry, Slough, England

[73] Assignee: Alusuisse Holdings AG, Neuhausen Am Rheinfall, Switzerland

[*] Notice: The term of this patent shall not extend beyond the expiration date of Pat. No. 5,641,639.

[21] Appl. No.: 466,035

[22] Filed: Jun. 6, 1995

Related U.S. Application Data

[63] Continuation of Ser. No. 144,870, Nov. 3, 1993, Pat. No. 5,641,639, which is a continuation of Ser. No. 971,254, Nov. 4, 1992, abandoned, which is a continuation of Ser. No. 728,029, Jul. 8, 1991, abandoned, which is a continuation of Ser. No. 295,100, Feb. 22, 1989, abandoned.

[30] Foreign Application Priority Data

Apr. 29, 1987 [GB] United Kingdom ............ 8710098
Apr. 29, 1987 [GB] United Kingdom ............ 8710099

[51] Int. Cl.⁶ ................ G01N 33/543; G01N 33/558
[52] U.S. Cl. .......... 435/7.92; 422/56; 435/7.93; 435/25; 435/27; 435/28; 435/962; 435/963; 435/970; 436/501; 436/514; 436/518; 436/530; 436/810; 436/817
[58] Field of Search ............ 435/7.92, 25, 27, 435/28, 962, 963, 970, 975, 7, 93; 436/501, 514, 518, 530, 810, 817; 422/56

[56] References Cited

U.S. PATENT DOCUMENTS

| | | | |
|---|---|---|---|
| 4,690,907 | 9/1987 | Hibino et al. | 436/514 |
| 4,837,395 | 6/1989 | Leeder et al. | 435/7 |
| 4,857,453 | 8/1989 | Ullman et al. | 435/7 |
| 4,861,711 | 8/1989 | Friesen et al. | 435/7 |
| 5,073,484 | 12/1991 | Swanson et al. | 435/7.92 |
| 5,104,793 | 4/1992 | Buck | 435/7.92 |
| 5,500,350 | 3/1996 | Baker et al. | 435/7.92 |
| 5,641,639 | 6/1997 | Perry | 435/7.92 |

FOREIGN PATENT DOCUMENTS

| | | |
|---|---|---|
| 0 094 777 | 11/1983 | European Pat. Off. |
| 0 148 643 | 7/1985 | European Pat. Off. |
| 0 202 081 | 11/1986 | European Pat. Off. |
| 0 225 054 | 6/1987 | European Pat. Off. |
| 2 029 011 | 3/1990 | United Kingdom . |
| 86/04683 | 8/1986 | WIPO . |

OTHER PUBLICATIONS

Aldrich Chemical Company, Inc. Catalog, 1990, pp. 491 and 672.
Worthington Enzyme Manual, Worthington Biochemical Corporation, 1972, p. 43.

*Primary Examiner*—David Saunders
*Attorney, Agent, or Firm*—Venable; John W. Schneller

[57] ABSTRACT

A device for performing an enzyme-labelled binding assay comprises an absorbent material and a developing solution containing a substrate for said enzyme, wherein the absorbent material is provided with a plurality of reagent zones including an indicator reagent zone and is capable of transporting the developing solution by capillary action sequentially through the reagent zones, and wherein the indicator reagent zone includes a reagent capable, directly or indirectly, of immobilizing an enzyme-labelled reagent in an amount dependent on the assay result, characterized in that the absorbent material includes a reagent that prevents a signal formation except where enzyme-labelled reagent is immobilized at the indicator reagent zone. The absorbent material is suitably in the form of an elongate strip provided with transverse reagent zones. The device is useful for performing immunoassays, including immunometric assays and dual analyte assays.

18 Claims, 3 Drawing Sheets

BINDING ASSAY METHOD USING A SIGNAL PREVENTING REAGENT

FIELD OF THE INVENTION

This is a continuation of application Ser. No. 08/144,870, filed Nov. 3, 1993 and now U.S. Pat. No. 5,641,639, which is a continuation of Ser. No. 07/971,254, filed Nov. 4, 1992 and now abandoned, which is a continuation of application Ser. No. 07/728,029, filed Jul. 8, 1991 and now abandoned, which is a continuation of application Ser. No. 07/295,100, filed Feb. 22, 1989 and now abandoned, filed as PCT/GB88/00329 Apr. 28, 1988.

This invention relates to a device for performing an enzyme-labelled binding assay.

More particularly, the device comprises an absorbent material and a developing solution, the absorbent material being capable of transporting the developing solution by capillary action, and being provided with a reagent which only allows the interaction of an enzyme-labelled reagent and substrate to generate a detectable signal at an indicator reagent zone, the latter including a reagent capable, directly or indirectly, of immobilising the enzyme-labelled reagent in an amount dependent on the assay result.

BACKGROUND TO THE INVENTION

Binding assays such as immunoassays, are in widespread use in clinical laboratories for the detection of substances in biological fluids. There is however increasing interest in the development of assays which can be performed without the need for complex analytical techniques and equipment, for example, by a physician in his consulting room or by a patient at home. Such assays are not only more convenient but allow savings in time and expense. Particular applications for which convenient and simple assays and reagent formulations are being sought are the detection of pregnancy and for the determination of the fertile period of the menstrual cycle.

Binding assays have been described which employ a strip of material provided with a plurality of reagent zones, in which a developing solution forms a solvent front which passes along the strip by capillary action picking up and facilitating reaction between a sample and assay reagents located at the reagent zones (see for example, British patent specification 1589234). A feature of such strips is the existence of a test location at which, under certain conditions determined by the assay protocol and the sample composition, a labelled reagent becomes immobilised, giving an indication of the assay result. In early assays, the labelled reagent was a binding partner or analogue of the analyte to be measured, labelled with a radioactive isotope. Such assays require instrumentation to detect the level of radioactive label and may present health risk problems. A solution to this has been the use of enzyme labels which produce a characteristic signal (such as a calorimetric signal) with an appropriate substrate.

A significant problem in the design of such so called "dipstick" enzyme-labelled binding assays is the application of the appropriate enzyme substrate in order to produce a detectable signal. The signal may be developed by adding substrate to the appropriate position on the reagent strip after allowing the assay to proceed to completion. Alternatively, the appropriate part of the strip may be removed and chemically analysed. All of these represent steps which would be at least inconvenient, if not impossible for home use of the assay.

In our European Patent Specification No. 225054 we describe a device for conducting competitive and non-competitive enzyme-labelled binding assays which greatly facilitates the use of such assays in the home, with a minimum of manipulative steps. The device may essentially employ an elongate strip, usually of a bibulous paper, and a reservoir. Arranged transversely in order along the strip there may be for example a sample receiving zone, a reagent zone which is impregnated with a suitable enzyme-labelled hapten or antibody for the particular assay protocol in use, and an indicator reagent zone which is capable of immobilising the enzyme-labelled reagent. The reservoir, which may be a rupturable sac, is at the end of the strip adjacent to the sample receiving zone and contains a developing solution which comprises buffer and a signal-producing substrate, together with any necessary cofactors, for the enzyme-labelled reagent. The enzyme and substrate are chosen such that when in contact they produce a signal, such as colour formation which may be readily determined. For other assay protocols the nature of the reagent zone and developing solution may be modified, and additional reagent zones may be present, as appropriate.

By way of an example, when the device is used for a competitive hapten assay, a sample is applied to a sample receiving zone and the reservoir is ruptured such that developing solution containing the signal-producing substrate together with any necessary cofactors enters the strip and moves along it by capillary action, picking up the sample and the enzyme-labelled hapten fromthe respective zones, and transporting them and the signal-producing substrate and any cofactors to the indicator zone where the enzyme labelled hapten and hapten from the sample compete for binding sites on an immobilised antibody.

In a particularly useful form of the device the signal-producing substrate, or any necessary cofactors, are chosen such that they migrate more slowly along the strip than the enzyme-labelled reagent. In this way, no signal is formed until the indicator zone when the signal-producing substrate and cofactor meets any bound enzyme-labelled reagent. This differential migration avoids any obscurity in the assay, from incomplete separation of the signal resulting from bound and unbound enzyme-labelled hapten, which can occur when the substrate and enzyme-labelled hapten move along the strip together to the indicator zone. The intensity of the signal at the indicator zone is inversely proportional to the concentration of the hapten in the sample.

SUMMARY OF THE INVENTION

We have now found a new device for performing enzyme-labelled binding assays, in which in a preferred aspect signal-producing substrate and enzyme-labelled reagent co-migrate, thus avoiding any use of differential migration, but which still ensures that a clear result is obtained. The device is convenient to operate, with a minimum of manipulative steps, and is particularly suitable for use in the home.

Thus, according to one aspect of the present invention, we provide a device for performing an enzyme-labelled binding assay, the device comprising an absorbent material and a developing solution containing a substrate for said enzyme, wherein the absorbent material is provided with a plurality of reagent zones including an indicator reagent zone and is capable of transporting the developing solution by capillary action sequentially through the reagent zones, and wherein the indicator reagent zone includes a reagent capable, directly or indirectly, of immobilising an enzyme-labelled reagent in an amount dependent on the assay result, characterised in that the absorbent material includes a reagent that prevents a signal formation except where enzyme-labelled reagent is immobilised at the indicator reagent zone.

In the device according to the invention, the assay may be any type of enzyme-labelled binding assay in which the amount of an enzyme-label immobilised in an indicator reagent zone is indicative of the result of the assay. The signal produced in the indicator reagent zone by the action of the immobilised enzyme may be fluorometric or chemiluminometric but is preferably calorimetric. The device may be of use for example in clinical chemistry and microbiology, in particular for use in fertility and nucleic acid determinations and for the diagnosis of infectious diseases. The device is suitable for conducting competitive and non-competitive binding assays in which analyte in the sample either binds to an enzyme-labelled reagent or binds to a reagent in competition with an enzyme-labelled analyte analogue, or possesses a characteristic which is itself measurable, and binds to a reagent immobilised on the device. Preferably, the assay is an immunoassay.

The assay may be for example a two site immunometric assay or a dual competition assay such as a dual analyte assay of the type described in UK patent specifications 2029011B and 2116318B. The analyte may be any analyte which has a specific binding partner, for example an antibody or antigen able to bind with an antigen or antibody or a single stranded nucleic acid able to bind with a complementary nucleic acid strand.

The enzyme-labelled reagent may be any enzyme capable of producing a measurable signal in the presence of an appropriate substrate, (hereinafter referred to as the signal producing enzyme) coupled to a hapten, antibody or nucleic acid as appropriate. Alternatively, the enzyme in the enzyme-labelled reagent may be an enzyme capable of producing a substrate for a signal producing enzyme (hereinafter referred to as the substrate-producing enzyme). Thus, in general the signal-producing enzyme may be an oxidoreductase, such as a peroxidase, e.g. horseradish peroxidase, an oxidase, e.g. citrate synthase, uricase, or monoamine oxidase, or a dehydrogenase such as a diaphorase or glucose-6-phosphate dehydrogenase; or a hydrolase such as a phosphatase, e.g. alkaline phosphatase, a glycosidase, e.g. β-glucosidase or β-galactosidase, or a cholinesterase. The substrate-producing enzyme may for example be an oxidase such as glucose oxidase, or a phosphatase such as alkaline phosphatase.

Depending on the assay in use, the signal-producing enzyme or substrate-producing enzyme may be covalently attached for example to a hapten, antibody or nucleic acid using standard coupling procedures, for example sulfhydryl-maleimide coupling [Ishikawa, E., (1980), Immunoassay suppl. 1, 1–16; Duncan, R. J. S. et al, Anal. Biochem., 132, 68–72], disulphide thiol exchange [Carlsson, J., et al, (1978), Biochem, J., 173, 723–737], periodate oxidation [Nakane, P. K., et al (1974), J. Histochem. Cytochem, 22, 1084–1091] or glutaraldehyde coupling [Avrameas, S. (1969), Immunochem., 6, 43–72); Avrameas, S., et al, (1971), Immunochem, 8, 1175–1179].

Alternatively, the signal-producing or substrate-producing enzymes may not form part of the enzyme-labelled reagent, but may be immobilised in the absorbent material, for example at the indicator reagent zone, using physical adsorption or chemical coupling as discussed below in relation to antibody immobilisation. Thus, for example, when the assay system utilises both a signal-producing enzyme and a substrate-producing enzyme the former may be immobilised at the indicator reagent zone and the latter may be attached to an antibody, hapten or nucleic acid to form the enzyme-labelled reagent.

The signal-producing substrate may in general be any compound that produces a detectable signal either through the direct or indirect action of the signal-producing enzyme. Thus, the signal-producing substrate may itself be transformed by the action of the signal-producing enzyme (e.g. by oxidation, reduction or hydrolysis) to yield a detectable product (e.g. detectable by colorimetric, fluorometric or chemiluminometric means). Examples of such substrates are phenols, e.g. nitrophenol esters, indoles, e.g. indole esters, benzidines, e.g. tetramethylbenzidine and coumarins e.g. hydroxycoumarin esters, which may be converted to coloured products by the action of an appropriate enzyme.

Alternatively, the signal-producing substrate may be a compound that is converted to a detectable product by interaction with a further compound produced by the signal-producing enzyme. Thus, for example, the signal-producing substrate may be an electron acceptor such as a tetrazolium salt or a reagent such as Ellman's reagent (5,5-dithiobis-(2-nitrobenzoate)), which reacts in the presence of an electron donor, for example nicotinamide adenine dinucleotide (NAD) or coenzyme A (CoA) to form a detectable product. The electron donor may be generated by the action of the signal-producing enzyme on the corresponding electron acceptor, for example reduced NAD (NADH) may be oxidised to NAD and acetyl CoA may be oxidised to CoA by appropriate enzymes.

In general, the product formed from the signal-producing substrate will be relatively insoluble in water and will bind to the absorbent material so as to provide a detectable signal where it is formed at or about the indicator reagent zone.

Where desired, the sensitivity of the signal-producing system may be increased by selecting reagents which interact to form an amplification system. Such reagents may be for example a series of interacting enzymes (an enzyme cascade) included in the developing solution or immobilised in the absorbent material. Thus for example the enzyme-labelled reagent may form the primary enzyme in the cascade and act on an inactive precursor compound converting it to an active entity (for example a proenzyme-enzyme conversion, e.g. trypsinogen-trypsin and chymotrypsinogen-chymotrypsin conversions). The active entity generated can then be used to activate inactive precursor and so on until the final reaction is used to generate a measurable end-point, e.g. a coloured product. Amplification is achieved by the ability of any given component of the cascade to activate a large excess of the next component in the cascade sequence. The signal-preventing reagent will be used at any suitable point in the amplification system for example to prevent interaction of the enzyme-labelled reagent with the first inactive precursor until the enzyme-labelled reagent is immobilised at the indicator reagent zone.

Specific examples of signal-producing systems which may be used in the device according to the invention are given in Table 1 below.

TABLE 1

Examples of Signal Producing Systems

| SIGNAL-PRODUCING ENZYME | SIGNAL-PRODUCING SUBSTRATE | CO-SUBSTRATE/ ACTIVATOR | SUBSTRATE-PRODUCING ENZYME(S) | SUBSTRATES(S) FOR SUBSTRATE PRODUCING ENZYME(S) |
|---|---|---|---|---|
| Horseradish peroxidase[+] | Tetramethylbenzidine | $H_2O_2$ | — | — |
| Diaphorase[+] | A tetrazolium salt e.g. 2,3,5-triphenyl-tetrazolium chloride | NADH | — | — |
| Horseradish peroxidase* | Tetramethylbenzidine | — | Glucose Oxidase[+] | Glucose |
| Horseradish peroxidase* | Tetramethylbenzidine | — | Glucose Oxidase[+] and Alkaline Phosphatase[+] | Glucose-6-phosphate |
| Alkaline Phosphatase[+] | 4-nitrophenyl phosphate or 5-bromo-4-chloro-3-indolyl phosphate | Magnesium ion Manganese ion | — | — |
| β-Galactosidase[+] | 2-nitrophenyl-β-D-galactopyranoside or 5-bromo-4-chloro-3-indolyl-β-D-galactopyranoside | — | — | — |

| SIGNAL-PRODUCING REAGENT | SIGNAL-PRODUCING SUBSTRATE | CO-SUBSTRATE/ ACTIVATOR | SUBSTRATE-PRODUCING ENZYME(S) | SUBSTRATES(S) FOR SUBSTRATE PRODUCING ENZYME(S) |
|---|---|---|---|---|
| Alkaline Phosphatase[+] | 4-nitrophenyl phosphate or 5-bromo-4-chloro-3-indolyl phosphate | Magnesium ion Magnesium ion | — | — |
| Citrate Synthase[+] | 5,5,dithiobis-(2-nitrobenzoate) | Coenzyme A (CoA) | — | acetyl CoA/ oxaloacetate |

[+]Enzyme forms enzyme-labelled reagent
*Enzyme is immobilised at indicator reagent zone The exact nature of the reagent that prevents a signal formation except where enzyme-labelled reagent is immobilised at the indicator reagent zone (hereinafter referred to as the signal preventing reagent) will depend on the assay system in use, but in general the reagent may be any reagent that prevents the effective interaction of the enzyme-substrate pair.

Thus, for example the signal-preventing reagent may be (1) a reversible inhibitor of the enzyme-labelled reagent (2) a further enzyme or a reagent which will compete with the enzyme-labelled reagent for substrate or cofactors; (3) an alternative substrate for the enzyme-labelled reagent which is not chromogenic and competes with the signal-producing substrate for the enzyme; (4) an end-product of a reaction catalysed by the enzyme-labelled reagent which is able to inhibit the enzyme; or (5) a reagent which is able to maintain the pH in the locality of the enzyme-labelled reagent away from the pH optimum of the enzyme.

Thus, for example, a Type (1) signal preventing reagent may be any appropriate reversible inhibitor of the enzyme, such as adenosine triphosphate when the enzyme is citrate synthase. A Type (2) reagent may be any appropriate enzyme or reagent that competes with the enzyme-labelled reagent, such as a reductase, (e.g. catalase) or a reducing agent (e.g. ascorbic acid or a salt thereof such as sodium ascorbate; or reduced glutathione) when the enzyme is an oxidoreductase e.g. horseradish perooxidase, or an oxidase, e.g. glucose oxidase. Reducing agents, especially ascorbic acid or a salt thereof are particularly useful when the enzyme is an oxidoreductase. Sodium ascorbate is particularly preferred. A Type (3) reagent may be any appropriate alternative substrate for the enzyme, such as an appropriate phosphate ester, (e.g. esters of primary or secondary alcohols, sugar alcohols, cyclic alcohols, phenols and amines, and, especially, glucose-6-phosphate or nicotinamide adenine dinucleotide phosphate) when the enzyme is a phosphatase, or lactose when the enzyme is a glycosidase such as β-galactosidase. A Type (4) reagent may be any appropriate end-product of a reaction catalysed by the enzyme, such as orthophosphate when the enzyme is a phosphatase such as an alkaline phosphatase. A Type (5) reagent may be any appropriate reagent(s) that can maintain the pH at a value away from the optimum pH value of the enzyme, such as a reagent(s) that raises the pH by generating alkaline products (e.g. urease and urea, that together generate ammonia) and a reagent(s) that lowers the pH by generating acid products (e.g. penicillinase and penicillin G, that together generate penicilloic acid).

Alternatively, the signal-preventing reagent may be any compound, or compounds, which are capable of immobilising, either by physical or chemical means, the signal-producing substrate or, when in use, a substrate for a substrate-producing enzyme or derivatives thereof, or any co-substrate for said enzyme.

The quantity of signal-preventing reagent used will be such that at no time during the operation of the assay, except when enzyme-labelled reagent is immobilised in the indicator reagent zone,can the enzyme and signal-producing substrate interact to form a signal at the indicator reagent zone. In general, the concentration of signal-preventing reagent used will need to be determined empirically for each assay device, and will depend on factors such as the concentration of the signal-producing enzyme and signal-producing substrate present and their relative affinities for each other and for the signal-preventing reagent. In general, however, except at the indicator reagent zone, the signal-preventing reagent will usually be in excess concentration relative to the concentrations of signal-producing enzyme and signal-producing substrate.

The absorbent material, which may be in the form of an elongate strip, may be any material capable of transporting the developing solution by capillary action. A preferred material is a bibulous paper, such as a glass fibre paper, although any material exhibiting the necessary capillary property and a low level of non-specific binding could be used.

In order that the physical dimensions of the absorbent material are not excessive, the enzyme-labelled reagent or enzyme-labelled reagent complexed with a co-migrating antigen should preferably exhibit an $R_f$ value of not less than 0.7.

The absorbent material may be impregnated with the signal preventing reagent and other reagents for the particular assay protocol, such that these may be present as discrete zones in or on the material. If desired, more than one reagent may be present in any particular zone, for example signal-preventing and enzyme labelled reagents may be present together in one zone.

Where the indicator reagent zone comprises an immobilised antibody, the immobilisation may be accomplished by physical adsorption or chemical coupling of the antibody to the strip using techniques well known in the art (see R. Axen et al, (1967), Nature 214, 1302; S. Avrameas and T. Ternynck (1965), Immunochemistry, 6 53; G. S. Bethell et al (1979), J. Biol. Chem., 254, 2672; and J. M. J. Frechet, (1981), Tetrahedron, 37, 663).

A preferred technique however is to attach the antibody to insoluble particles which are of the correct size or nature to be trapped within the framework, or adsorbed to the fibres, of the absorbent strip material and thus unable to move with the developing solution. A suitable type of particle is Eupergit ClZ, supplied by Rohm Pharma GmbH, Weiterstadt, West Germany. The antibody may be attached to the particles using standard procedures, for example as described in Example 1 below, and the particles with attached antibody then added to the absorbent material, for example, as a slurry.

The reagent zones may be generally arranged such that the developing solution contacts them sequentially. The order in which the reagent zones are arranged may be varied, except that when the signal-preventing reagent is in a separate zone to the enzyme labelled reagent, the signal-preventing reagent zone will always be the first of the two zones to be contacted by the developing solution. The reagent zones may be arranged on or in the material to allow for a predetermined incubation period between contact with adjacent reagent zones.

In the preferred form of the device, the absorbent material is in the form of an elongate strip with transverse reagent zones. The device may also comprise an elongate strip, attached at its terminal end to a pad of absorbent material.

The developing solution in the device according to the invention may contain the signal-producing substrate or, alternatively, when a substrate-producing enzyme is in use, a substrate for said enzyme. The developing solution may be the sample itself to which said substrate is added, but is preferably separate from the sample. Advantageously the solution is contained in a rupturable sac adjacent to part of the absorbent material, suitably at one end of a strip of absorbent material. In the alternative, the device of the invention may be in the form of a kit comprising separately an absorbent material and a container of the developing solution, as defined. Preferably, the developing solution comprises a buffer compatible with the assay system. A particularly preferred developing solution for an enzyme labelled immunoassay comprises 0.1M acetate-citrate (pH 6) containing 0.2% (v/v) Tween 20 and the signal-producing substrate or substrate for the substrate-producing enzyme as appropriate.

The device may include a sample receiving zone which can, if desired, be provided with a filter member, such as a filtration pad, to remove solid material such as cellular material and debris.

The device of the invention may include an assay completion indicator zone comprising immobilised enzyme to indicate completion of the assay. Where the absorbent material is in the form of a strip, the assay completion indicator zone is preferably located near the end of the strip remote from the end at which the developing solution is applied.

The absorbent material may be enclosed within a non-transparent covering except in the indicator reagent zone where a transparent window may be provided. Access to the sample zone may be provided by removal of a resealable plug which can be replaced after application of the sample. Application of a sample to the device may be by way of an applicator which delivers a predetermined volume of the sample, for example a sampling loop.

The device may be individually packaged, but for easy monitoring, for example of daily urine samples over the menstrual cycle in the home, a plurality of devices of the invention may be packaged together. We further provide therefore a test sheet comprising a plurality of devices of the invention.

In general use, when signal-preventing reagent is intended to migrate with enzyme-labelled reagent, the developing solution is first applied to the absorbent material. For example, where the absorbent material is in the form of a strip, the developing solution is applied to one end of the strip, advantageously by rupturing a sealed sac, for example, by finger pressure, to release the contents. The developing solution advances through the absorbent material, picking up sample applied at the sample receiving zone, and the signal-preventing reagent and other reagents, including an enzyme-labelled reagent, present as reagent zones in the material. The assay reactions take place in the advancing solvent front of the developing solution but no signal is produced due to the presence of the signal-preventing reagent. After an incubation period determined by the spatial separation of the reagent zones, an amount of the enzyme-labelled reagent is immobilised in the indicator reagent zone in an amount dependent upon the assay result. The signal-preventing reagent is not immobilised, but is washed through and out of the indicator reagent zone by the developing solution. Continued washing with developing solution removes the signal-preventing reagent from the indicator reagent zone and allows any immobilised enzyme in the zone to react with the substrate, thus generating a signal.

Preferably the signal-preventing reagent will migrate with the enzyme labelled reagent. However the signal-preventing reagent may be immobilised in the absorbent material by physical adsorption or chemical coupling, for example, as discussed above in relation to antibody immobilisation, at a location such that the developing solution reaches the signal-preventing agent before reaching the enzyme-labelled reagent. The quantity of signal-preventing reagent immobilised is such that after a finite period of time the reagent either becomes saturated with substrate so that no further substrate binding can occur, or is consumed by the substrate so that no further substrate metabolism occurs. In this way, a substrate free zone is created immediately behind the solvent front, the extent of which will be dependent on the time taken for the signal-preventing reagent to become saturated or consumed. The exact quantity of signal-preventing reagent used will depend on the assay system in use and will need to be determined empirically using preliminary small scale tests in accordance with conventional practice. In general, the quantity used will determine the extent of the substrate-free zone.

When the signal preventing reagent is immobilised in the absorbent material it may react either directly or indirectly with the substrate. Thus, for example, the signal-preventing reagent may be an antibody such as a monoclonal antibody which binds to a hapten to which the substrate has been covalently attached using conventional techniques. Alternatively the signal-preventing reagent may be a compound which interacts with a derivative of the substrate, for example the signal-preventing reagent may be streptavidin, and the substrate may be a biotinylated derivative (i.e. biotin covalently bound to the substrate using conventional techniques). In another alternative, the signal preventing reagent may be any compound capable of interacting directly with the substrate, for example the signal preventing reagent may be concanavalin A when the substrate is glucose.

The result of an assay as indicated by the device of the invention may be qualitative, read simply by the absence or presence of a signal, especially a coloured signal at the indicator reagent zone. This type of result may be, for example, of considerable use where a threshold value of a particular analyte in a sample is being monitored (such as the level of a particular hormone). However, the device can be employed to provide quantitative assay results. The intensity of the signal produced at the indicator reagent zone will be either proportional to or inversely proportional to the concentration of analyte present in the sample. Thus, the indicator reagent zone of the device may, following an assay, be inserted into a reflectance spectrophotometer, or a fluorimeter (if the signal produced is fluorescent), to measure the intensity of the signal produced.

BRIEF DESCRIPTION OF THE DRAWINGS

The invention is now described by way of example with reference to the accompanying drawings in which.

Embodiments of the invention are described first generally with reference to FIGS. 1 to 6 and then more specifically with reference to Examples 1–3.

The materials and methods described below in relation to Example 1 are also examples of materials and methods which may be used in the general embodiments discussed below in relation to FIGS. 1–6.

MIXED STEROID ANTIGEN (MSA)

Mixed steroid antigen (MSA) is a bifunctional ligand comprising oestrone-3-glucuronide (E13G) and pregnanediol-3-glucuronide (PD3G). The synthesis of the compound is described in British Patent Specification GB-B-2116318.

Figure 1:
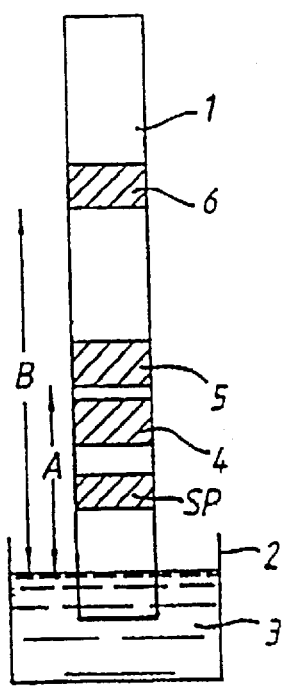
FIG. 1—shows a device for conducting a competitive hapten assay.

FIG. 1 shows a device for measuring the concentration of pregnanediol-3-glucuronide (PD3G) in a urine sample using a competitive hapten assay protocol. Referring to FIG. 1, the device comprises a strip, 1, of a bibulous paper and a reservoir, 2, containing a developing solution, 3, consisting of a substrate-buffer. The strip is provided with a signal-preventing reagent zone, SP, a sample receiving zone, 4, a first reagent zone, 5 and a second, indicator, reagent zone 6. The signal-preventing reagent zone, SP, includes a signal-preventing reagents and the first reagent zone, 5, includes enzyme-labelled PD3G comprising PD3G hapten covalently attached to a signal-producing or substrate-producing enzyme. The signal-preventing reagent and enzyme-labelled PD3G are each impregnated into the strip, such that, in use, they are caused to dissolve and migrate through the strip by passage of the developing solution through the strip. The indicator zone, 6, comprises antibody to PD3G and, where necessary, signal-producing enzyme, covalently bonded to the strip. Table 1 includes examples of suitable alternative enzymes, substrates and signal-preventing reagents for use in the assay.

In use, a sample of urine is applied to the sample receiving zone, 4, and the developing solution, 3, is released onto the end of the strip by rupturing the reservoir, 2, with finger pressure. The developing solution, 3, passes through the strip by capillary action picking up the signal-preventing reagent, sample and the enzyme-labelled PD3G in the solvent front, from the signal-preventing reagent zone, SP, the sample receiving zone, 4, and the first reagent zone, 5, respectively.

When the solvent front of the developing solution, 3, reaches the first reagent zone, 5, signal-preventing reagent, substrate, and enzyme-labelled PD3G are present in the solvent front, together with any PD3G derived from the sample. No signal is formed at this stage, however, or as the solvent front subsequently transports the reagents to the indicator reagent zone 6, since the signal-preventing reagent acts to stop the interaction of the substrate and enzyme. When the solvent front reaches the indicator reagent zone, 6, any PD3G present from the sample competes with the enzyme-labelled PD3G for a limited number of binding sites in the indicator reagent zone. The amount of enzyme-labelled PD3G that becomes bound to the strip in the indicator reagent zone, 6, is therefore inversely proportional to the concentration of PD3G in the sample. Continued development of the strip washes the signal-preventing reagent, and any unreacted reagents through the indicator zone, 6, such that the zone becomes free of signal-preventing reagent. At the same time, the continued development brings fresh substrate into the indicator zone where in the absence of the signal-preventing reagent it is converted by the bound signal-producing enzyme and any necessary substrate producing enzyme to give a coloured product. The coloured product thus giving a sharp band of colour at the indicator zone, 6. The difference between distances B and A as shown in FIG. 1 is made relatively small as the sample and the enzyme-labelled PD3G do not interact until the indicator zone, 6, is reached thus allowing a reduction in the length of the strip. The duration of the competitive reaction which occurs at the indicator zone, 6, is equal to the time it takes for the sample and the enzyme-labelled PD3G to pass through theindicator zone, 6. This is determined by the physical properties of the material from which the strip is made.

Figure 2:
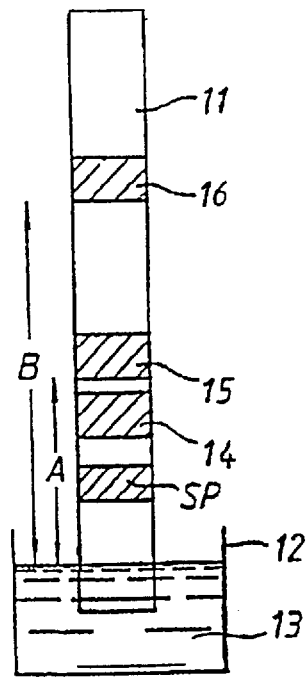
FIG. 2—shows a device for conducting a non-competitive hapten assay.

FIG. 2 shows a further device for measuring the concentration of PD3G in a urine sample using a non-competitive hapten assay protocol. Referring to FIG. 2, the device comprises a strip, 11, of a bibulous paper and a reservoir, 12, containing a developing solution, 13, consisting of a substrate-buffer. The strip is provided with a signal-preventing reagent zone, SP, a sample receiving zone, 14, a first reagent zone, 15, and a second, indicator, reagent zone, 16. The first reagent zone, 15, includes enzyme labelled anti-PD3G comprising antibody to PD3G covalently attached to a signal-producing or substrate-producing enzyme, the enzyme-labelled anti-PD3G being impregnated into the strip such that, in use, it is caused to migrate through the strip by passage of the developing solution, 13, through the strip. The indicator zone, 16, comprises PD3G and, where necessary, signal-producing enzyme, covalently bonded to the strip. The reservoir, 12, the developing solution, 13, the signal-preventing reagent and the enzyme-label are as described above with reference to FIG. 1.

In use, a sample of urine is applied to the sample receiving zone, 14, and the developing solution 13, is released onto the end of the strip by rupturing the sac, 12, with finger pressure. The developing solution, 13, passes through the strip by capillary action picking up the signal-preventing reagent and sample. Any PD3G present in the sample is bound in the first reagent zone, 15, by the enzyme-labelled anti-PD3G which is present in excess. the incubation time for this interaction to take place is controlled by the difference between distances B and A as shown in FIG. 2. As the solvent front contacts the indicator zone, 16, PD3G covalently bonded to the strip binds any unreacted enzyme-labelled antibody to PD3G. Again, since the signal-preventing reagent moves through the strip with the enzyme-labelled anti-PD3G and substrate, colour generation only occurs at the indicator zone, 16, where the signal-producing enzyme and any necessary substrate-producing enzyme has been immobilised and when the signal-preventing reagent has been washed out of the zone.

Figure 3:
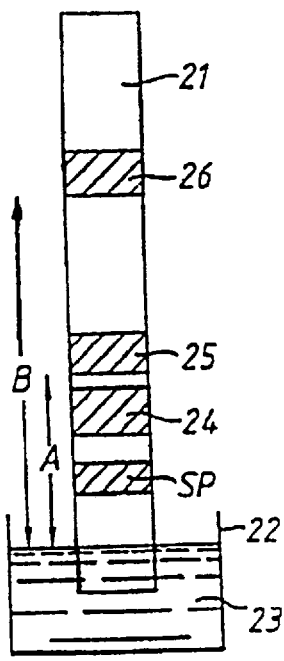
FIG. 3 shows a device for conducting a two-site sandwich, or immunometric assay.

FIG. 3 shows a device for detecting a given concentration of thyroid stimulating hormone (TSH) in a sample using a two-site sandwich assay or immunometric assay protocol. Referring to FIG. 3 the device comprises a strip, 21, of a bibulous paper and a reservoir, 22, containing a developing solution, 23, consisting of a substrate-buffer. The reservoir, 22, and developing solution, 23, are as described above with reference to FIG. 1. The strip is provided with a signal-preventing reagent zone, SP, a sample receiving zone, 24, a first reagent zone, 25, and a second, indicator, reagent zone, 26. The first reagent zone, 25, includes enzyme labelled anti-TSH comprising antibody to TSH covalently attached to a signal-producing or substrate-producing enzyme, the enzyme-labelled anti-TSH being impregnated into the strip, 21, such that, in use, it is caused to migrate through the strip by passage of the developing solution, 23. The indicator zone, 26, comprises a second antibody to TSH and, where necessary, a signal-producing enzyme covalently bonded to the strip, 21. The second antibody has specificity for a different and non-competing epitope of TSH from that of the enzyme-labelled antibody. The signal-preventing reagent and the enzyme label are as described above with reference to FIG. 1.

In use, any TSH present in the sample is bound by the enzyme-labelled antibody which is present in excess as they co-migrate through strip. The time allowed for this first reaction is governed by the difference between the distances B and A as shown in FIG. 3. On passing through the indicator zone, the TSH (in the form of an antibody complex) is bound by the second antibody. The time of the second incubation is governed by the speed of capillary migration of the solvent front through the material of the strip. Again, colour development only occurs where signal-producing enzyme and any necessary substrate-producing enzyme is immobilised in the indicator zone and signal-preventing reagent has been washed out of the zone.

Figure 4:
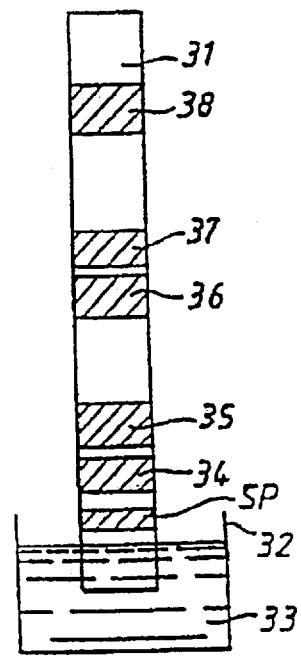
FIG. 4 shows a device for conducting a dual analyte assay.

FIG. 4 shows a device for measuring the ratio of the concentrations of PD3G and oestrone-3-glucuronide (E13G) in urine sample. The ratio of these two products has been shown to be indicative of the fertile period of the female menstrual cycle (see for example British published patent specifications GB-B-2029011 and GB-B-2116318).

Referring to FIG. 4, the device comprises a strip, 31, of bibulous paper and a reservoir, 32, containing a developing solution, 33, consisting of substrate-buffer. The reservoir, 32, and developing solution, 33, are as described above with reference to FIG. 1. The strip is provided with a signal-preventing reagent zone, SP, a sample receiving zone, 34, a first reagent zone, 35, a second reagent zone, 36, a third reagent zone, 37, and a fourth, indicator, reagent zone, 38. The first reagent zone, 35, comprises a mixed steroid antigen (MSA) consisting of a PD3G hapten and an E13G hapten covalently bonded to a bridging structure. The MSA is impregnated into the strip, 31, such that, in use, it may migrate through the strip in the advancing solvent front of the developing solution, 33. The second reagent zone, 36, comprises an antibody to E13G which may be free to migrate through the strip in the advancing solvent front though is preferably covalently bonded to the strip. The third reagent zone, 37, comprises an enzyme-labelled anti-E13G, impregnated into the strip, 31, such that it may migrate through the strip with the developing solution, 33. The fourth, indicator, reagent zone, 38, comprises antibody to PD3G covalently bonded to the strip. The signal-preventing reagent and enzyme label are as described above in relation to FIG. 1.

In use, a urine sample is applied to the sample zone, 34, and the reservoir, 32, of developing solution, 33, is ruptured, releasing the developing solution onto one end of the strip. The developing solution passes up the strip, 31, by capillary action picking up signal-preventing reagent from the signal-preventing reagent zone, SP, sample from the sample receiving zone, 34, and mixed steroid antigen from the first reagent zone, 35. The signal-preventing reagent, sample and MSA co-migrate along the strip to the second reagent zone, 36, at which the antibody to E13G is covalently immobilised. The MSA and E13G present in the sample compete for limited binding sites as they pass through the second reagent zone, 36. If the concentration of E13G in the sample is low, then a substantial proportion of the MSA is bound in the second reagent zone, 36, and cannot migrate further. if, however, the sample concentration of E13G is high, then the MSA will be free to migrate, together with the signal-preventing reagent and sample, to the next reagent zone, namely, the third reagent zone, 37, comprising enzyme-labelled antibody to E13G. This latter reagent is present in excess and is non-covalently absorbed to the strip, 31. The enzyme-labelled antibody binds to the MSA as they both migrate together along the strip with the signal-preventing reagent and sample to the fourth, indicator, reagent zone, 38, at which antibody to PD3G is covalently attached to the strip. At the fourth indicator reagent zones 38, any PD3G present in the sample competes with the MSA/anti-E13G complex for binding to a limited number of binding sites of the covalently immobilised anti-PD3G antibody. The enzyme-labelled immunocomplex will be bound at the indicator zone,38, only when the sample concentration of PD3G is low. The excess reagents together with the signal-preventing reagent are washed from the measuring location by continued development of the strip. Substrate washed into the indicator reagent zone, 38, by the continued development of the strip is then converted by the enzyme-labelled, antibody-bound MSA to a coloured product giving a clear positive signal. The assay can be tuned to give a positive response only when a predetermined elevated level of E13G coincides with a predetermined low level of PD3G. A further reagent zone (not shown) may be provided at a point remote from the reservoir, 32, which comprises covalently bound enzyme. This reagent zone gives an indication that substrate has migrated through the length of the strip, thus indicating that the assay has run to completion. The position of the zone along the strip is determined by the Rf value of the signal-preventing reagent.

Figure 5:
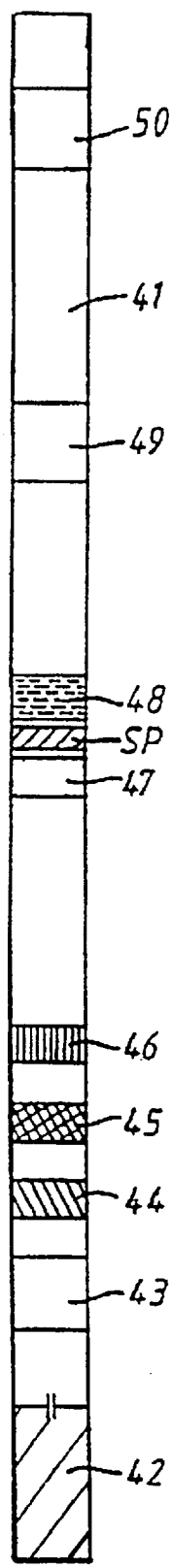
FIG. 5 shows a further device for conducting a dual analyte assay.

FIG. 5 shows a further device for measuring the ratio of the concentrations of PD3G and E13G in a urine sample.

Referring to FIG. 5, the device comprises a strip, 41, of bibulous paper and a reservoir, 42, containing a developing solution. The strip is provided with a sample receiving zone, 43, a first reagent zone, 44, a second reagent zone, 45, a third reagent zone, 46, a fourth reagent zone, 47, a fifth reagent zone, SP, a sixth reagent zone, 48, a seventh indicator reagent zone, 49 and an optional eighth, control indicator reagent zone, 50. The first reagent zone, 44, comprises anti-E13G (antibody to E13G). The second reagent zone, 45, comprises a mixed steroid antigen (MSA) as described in Example 4. The third reagent zone, 46, comprises biotin-labelled anti-PD3G (antibody to PD3G covalently bonded to biotin). The fourth reagent zone, 47, comprises dextran coated charcoal. The fifth reagent zone, SP, comprises a signal-preventing reagent. The sixth reagent zone, 48, comprises enzyme-labelled anti-E13G (antibody to E13G covalently bound to a signal-producing or substrate producing enzyme). The seventh reagent zone, 49, comprises immobilised streptavidin and any necessary signal-producing enzyme. The optional eighth reagent zone, 50, comprises an enzyme for the substrate in use.

The active components of the reagent zones are dried onto the strip as transverse bands. The streptavidin in the seventh test indicator, reagent zone, 49 is covalently attached to the strip and the dextran-coated charcoal in the fourth reagent zone, 47, is deposited onto the strip by adding an aqueous suspension of microparticulate charcoal and subsequently removing the water. All the other reagents are soluble and are impregnated into the strip by applying them each in solution and subsequently drying. The soluble reagents in use migrate with the solvent front of the developing solution. The reservoir, 42, comprises a rupturable sac containing the developing solution. The developing solution, signal-preventing reagents and enzyme-label are as described in relation to FIG. 1.

In use, a urine sample is applied to the sample receiving zone, 43, and the reservoir 42, of developing solution is ruptured, releasing the developing solution onto one end of the strip. The developing solution passes up the strip by capillary action, picking up sample from the sample receiving zone, 43, and in sequence, anti-E13G, MSA and biotin-labelled anti-PD3G. The soluble components of the assay pass through the strip in the advancing solvent front, and at the same time are mixed and allowed to react. The separation of the reagent zones may be adjusted to facilitate optimum incubation times for reaction. Unbound, low molecular weight species such as MSA and steroids are removed from the solvent front by the charcoal in the fourth reagent zone, 47. The solvent front passes through the fifth reagent zone, picking up the signal preventing reagent and the sixth reagent zone picking up the enzyme-labelled anti-E13G thus completing the assay protocol. The presence of complexes of enzyme-labelled anti-E13G/MSA/biotin-labelled PD3G is indicative of a high level of E13G and a dose level of PD3G. Such complexes are immobilised in the seventh test indicator, reagent zone, 49, by the interaction of biotin with immobilised streptavidin.

The developing liquid, as previously stated, includes a substrate for the enzyme-labelled reagent. The substrate has an $R_f$ value substantially the same as the enzyme-labelled species in the device, but will not react at the solvent front when the sixth reagent zone, 48, is reached because of the presence of the signal preventing reagent. As the solvent front meets and passes through the seventh, test indicator, reagent zone, 49 the signal preventing reagent will be washed clear of the zone by incoming fresh developing solution. However, if the complex including enzyme labelled anti-E13G has become immobilised, colour generation occurs in the seventh, test indicator, reagent zone. Thus colour in the seventh reagent zone indicates a positive test result. In an alternative, which is preferred, an eighth control indicator, reagent zone, 50, comprising enzyme for the substrate in use is provided to indicate arrival of the substrate at a predetermined part of the strip corresponding to completion of the assay.

Figure 6:
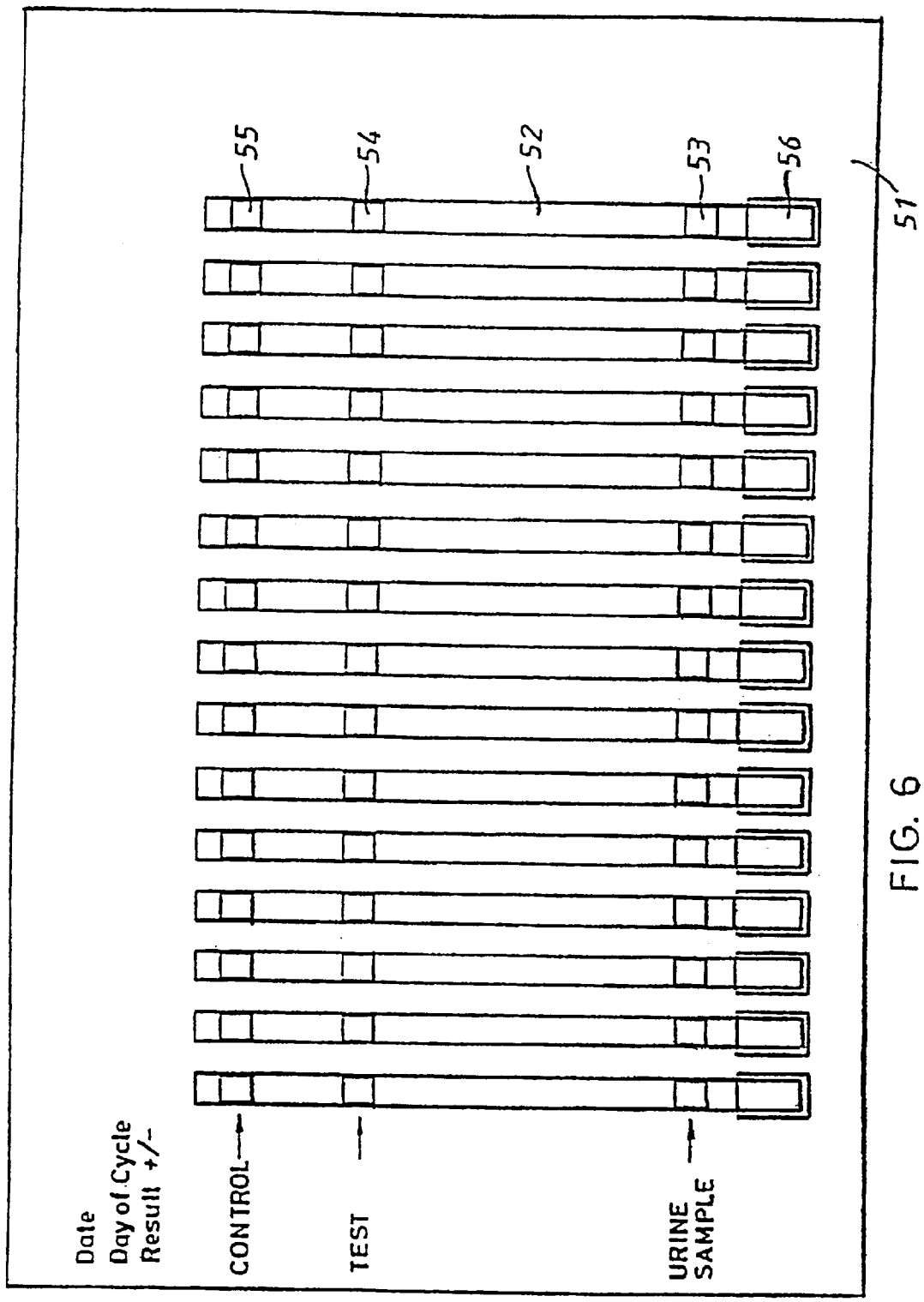
FIG. 6 shows a test sheet comprising a plurality of devices of the invention arranged to monitor the menstrual cycle.

FIG. 6 shows a test sheet for monitoring the menstrual cycle embodying a plurality of test strips as described above with respect to FIGS. 4 and 5.

Referring to FIG. 6, the test sheet comprises a rigid plastics backing plate or stand, 51, supporting a plurality of test strips of the invention, e.g. 52. (In the Figure, the details of the absorbent strips are not shown). In the embodiment shown, fifteen test strips are provided in side-by-side parallel arrangement. The backing plate or stand, 51, is overlaid with a plastics film, to cover the test strips, apart from in the sample receiving zones, 53. The plastics film (shown in FIG. 6 as transparent for clarity) is opaque in the test indicator zones, 54. The plastics film may be suitably masked or printed to indicate clearly the sample receiving and test indicator zones. The developing solution is contained in separate rupturable sacs, 56, one for each test strip.

In use, mid-stream urine is sampled using a disposable sample loop and an aliquot is blotted onto the sample receiving zone, 53, of a test strip, 52. The seal of a rupturable sac, 56, of developing solution is broken by finger pressure, thus initiating the test. After 15 to 20 minutes, the assay result is read from the test indicator zone, 54.

The presence of colour in the test zone indicates a positive result i.e. the woman is in, or near her fertile period. The converse applies with the absence of colour. For the woman who wishes to avoid conception, it is intended that she should test her urine once per day starting at about day 6 or 7 of her cycle. She should continue daily testing until a period of sustained positive results have been observed (more than 2 days) followed by a period of sustained negative results (more than 2 days). This would normally mean a total of 10 to 15 tests in a typical cycle. Whenever a positive result is observed, the woman should refrain from intercourse and should continue to do so until two successive daily negative results have been observed.

It is intended that colours developed in the strips are stable, and so form a semi-permanent record of the woman's cyclical activity.

EXAMPLE 1

Assay of Muscle/Brain Creatine Phosphokinase Isoenzyme (CPK-MB) Using a Two-site (Sandwich) Assay Unless otherwise stated, all reagents were obtained from Sigma Chemical Company, Poole, U.K.
Preparation of Strip
(a) Absorbent Strip Material
Gelman AP25 extra thick glass-fibre paper (15 cm×1 cm—from Gelman Sciences Inc., Ann Arbor, Mich., U.S.A.)
(b) Developing Solution (Substrate Buffer)
The developing solution was prepared as follows: To 1000 ml of sterile $DH_2 O$ was added:

2.5 g β-cyclodextrin 8.2 g sodium acetate 0.357 g citric acid 50 ul 30% $H_2O_2$ 100 ul tetramethylbenzidine (TMB) in dimethyl sulphoxide (DMSO) at 10 mg/ml.

5 g bovine serum albumin (BSA)*

1 ml Tween 20

5 g sodium chloride

*Sigma Chemical Company no. A8647, Fraction V
(c) Indicator Reagent Zone Solid-Phase Antibody to CPK-MB Buffer A. To 1000 ml of distilled $H_2O$ was added:

5.96 g $Na_2HPO_4$ 1.24 g $NaH_2PO_4$ 29.22 g NaCl

To 500 ul of Buffer (A) was added 3–4 mg of freeze-dried monoclonal antibody to CPK-MB and 125 mg of Eupergit ClZ (Rohm Pharma GmBH, Weiterstadt, West Germany). The reagents were mixed briefly and then left to stand at room temperature for 48 hours. The Eupergit was then resuspended in 20 ml of the following buffer (Buffer B).

Buffer B. To 1000 ml of distilled $H_2O$ was added:

5.96 g $Na_2HPO_4$ 1.24 g $NaH_2PO_4$ 3.75 g glycine

The Eupergit ClZ was allowed to settle at 4° C. for 12 hours. The supernatant was then aspirated off, and the Eupergit then resuspended in 20 ml of Buffer B and again allowed to settle. The supernatant was then again aspirated off, and the Eupergit/antibody resuspended in 12.5 ml of Buffer B. The supernatant was once again aspirated off and the Eupergit/antibody was added to 10 mm sodium phosphate buffer (pH 7.4) containing 5% BSA to form a 10% suspension. 50 μl of the suspension was then added to the Gelman paper (see Section (a)) 5 cm from one end to form the indicator reagent zone.
(d) Enzyme-Labelled Reagent Zone Antibody to CPK-MB—Peroxidase Conjugate Horseradish Peroxidase (HRP) was conjugated to a monoclonal antibody to CPK-MB using an adaption of the glutaraldehyde method of Avrameas (Immunochem., (1969),6, 43–72). The monoclonal antibody was chosen to recognise a different epitope to the monoclonal antibody used for the indicator reagent zone. 100 mg of HRP was dissolved in 500 ul of 0.05M bicarbonate buffer (pH 9.5) to which was added 500 μl of 11% (w/v) glutaraldehyde prepared in the same buffer. The reaction was conducted at room temperature (20°–25° C.) for two hours with gentle shaking. The reaction mixture was then applied to a PD10 column (Pharmacia Ltd.) which had previously been equilibrated with 0.05M bicarbonate buffer (pH 9.5). Elution was achieved with the same buffer and those fractions containing activated HRP were pooled. Antibody (2–3 mg/ml) in 0.05M bicarbonate buffer (pH 9.5) was added to the activated HRP to give a mass ratio of 6:1 of activated HRP to antibody. The reaction was conducted at 4° C. for 16–21 hours after which the antibody-HRP conjugate was purified by gel filtration, typically on a TSK G3000SW column (Toya Soda, Japan).

Antibody-HRP conjugate (25 μl–1 μg/ml in 5% BSA in 20 mM BES, pH 6.2) prepared as above was added to the Gelman paper prepared in (c) above to form the enzyme-labelled reagent zone 3 cm from the indicator reagent zone and 2 cm from the end of the paper.
(e) Signal-Preventing Reagent Zone 50 μl of ascorbic acid (0.1M) was added to the Gelman paper prepared in (d) above to form the signal-preventing reagent zone 1 cm from the end of the paper and 1 cm from the enzyme-labelled reagent zone.
(f) Development of Strip—Assay of Creatine Phosphokinase 50 μl of CPK-MB (Calbiochem, USA—120 ng/ml in 50% Foetal Calf Serum) was applied to the enzyme-labelled reagent zone of the Gelman strip prepared in (c)–(e) above. As a control, 50 μl of 50% Foetal Calf Serum was added to the enzyme-labelled reagent zone of an identically prepared strip. Each strip was then developed the full length with developing solution (b). Ten minutes after the developing solution had reached the top of each strip a blue colour was observed at the indicator reagent zone of the strip to which the creatine phosphokinase had been applied. No colour appeared in the other strip. The appearance of the blue colour at the indicator reagent zone showed that TMB in the developing solution had been oxidised by $H_2O_2$ in the presence of immobilised HRP. Thus the solid phase antibody applied at this zone had complexed with the creatine phosphokinase and antibody-HRP conjugate transported to the zone by the developing solution. The signal-preventing reagent (ascorbic acid) which had co-migrated with the substrates (TMB and $H_2O_2$) and HRP (reducing the $H_2O_2$ and making it unavailable for reaction with TMB, as shown by the absence of colour in any other part of the strip) had not been immobilised at the indicator reagent zone, but had been transported out of the zone by the continued development of the strip, thereby allowing the TMB, $H_2O_2$ and HRP to react to generate the observed blue signal.

EXAMPLE 1a

The above experiment was repeated except that the signal-preventing reagent was 50 μl of catalase, (BCL, Lewes, East Sussex, England) at 100 $\mu gml^{-1}$ in phosphate buffered saline containing 1% BSA. As above, only the CPK-MB containing strip gave a blue colour at the indicator reagent zone.

EXAMPLE 2

Assay of Streptoccus A. Antigen Using a Two-site (Sandwich) Assay
Preparation of Strip
a) Absorbent Strip Material Whatman GFD glass-fibre paper (15×1 cm). From Whatman Paper Ltd., Maidstone, Kent, England b) Developing Solution (Substrate Buffer)

As (b) of Example 1 c) Indicator Reagent Zone. Solid-phase Antibody to Streptoccus A. Antigen

Buffer A:

0.82 g sodium acetate 0.0357 g citric acid 1000 ml distilled water

To 5 mg of antibody to Streptococcus A. antigen was added Buffer A (45 ml) and Dynospheres SS-052-R [5 ml; Dyno Particles A-S, Lillestrom, Norway; supplied as 10% w/v slurry]. The reaction mixture was mixed end-over-end for 24 hours at room temperature. The beads were sedimented by centrifugation, the supernatant discarded and the beads resuspended in 50 mls of buffer containing 1% (w/v) bovine serum albumin (BSA). The sedimentation and resuspension process was repeated a further 4 times.

d) Enzyme-labelled Reagent Zone. Antibody to Streptococcus A. Covalently Attached to Horse Radish Peroxidase (HRP)

This antibody recognised a different epitope on the Streptococcus A. antigen to the antibody used for the indicator reagent zone.

The antibody was covalently attached to HRP using the methodology described in (d) of Example 1.

e) Signal-Preventing Zone 50 mM sodium ascorbate in distilled water.

(f) Development of the Strip. Assay of Streptococcus A. Antigen

The following reagents were added to the strip;

(i) 50 $\mu$l of 50 mM sodium ascorbate in distilled $H_2O$ applied 4 cm from the bottom of the strip.

(ii) 50 $\mu$l of antibody-peroxidase [5 $\mu$gml$^{-1}$ in buffer from (c) containing 1% BSA] applied 5 cm from the bottom of the strip (iii) 50 $\mu$l of solid phase antibody applied 6 cm from the bottom of the strip. 50 $\mu$l of Streptococcus A. antigen ($10^7$ Streptococcus group A. bacteria per ml in distilled $H_2O$ containing 0.1% Triton X 100) was applied to the enzyme-labelled reagent zone. As a control 50 $\mu$l of Streptococcus, C antigen ($10^7$ Streptococcus group C bacteria per ml in d$H_2O$ containing 0.1% Triton X 100) was added to the enzyme labelled reagent zone of an identically prepared strip. Each strip was then developed the full length with developing solution (b). Fifteeen minutes after the developing solution had reached the top of each strip, a blue colour was observed at the indicator reagent zone of the strip to which the Streptococcus A. antigen had been applied. No colour appeared on the strip to which the Streptococcus C antigen had been applied.

The appearance of the blue colour at the indicator reagent zone showed that TMB in the developing solution had been oxidised by $H_2O_2$ in the presence of immobilised HRP. Thus the solid phase antibody applied at this zone had complexed with the Streptococcus A. antigen and antibody-HRP conjugate transported to the zone by the developing solution. The signal-preventing reagent (ascorbic acid) which had co-migrated with the substrates (TMB and $H_2O_2$) and HRP (reducing the $H_2O_2$ and making it unavailable to reaction with TMB, as shown by the absence of colour in any other part of the strip) had not been immobilised at the indicator reagent zone, but had been transported out of the zone by the continued development of the strip, thereby allowing the TMB, $H_2O_2$ and HRP to react to generate the observed blue signal.

EXAMPLE 3

Assay of Progesterone Using a Competitive Assay

Preparation of the Strip (a) Absorbent Strip Material

As (a) of Example 2.

(b) Developing Solution.

As (b) of Example 1.

(c) Indicator Reagent Zone. Solid Phase Antibody to Progesterone.

Reagent A. Anti-progesterone antibody was linked to Dynospheres SS-OS2-R as in (c) of Example 2 where the anti-progesterone antibody replaced the antibody to Streptococcus A. antigen.

Reagent B. Bovine serum albumin (BSA) was linked to SS-052-R as in (c) of Example 2, except that BSA replaced the antibody to Streptococcus A. antigen.

The indicator reagent zone reagent was prepared by mixing Reagent A and Reagent B in a ratio of 1:10 (v/v).

(d) Enzyme-labelled Reagent Zone. Progesterone Covalently Linked to Horse Radish Peroxidase (HRP).

The progesterone-HRP conjugate was obtained from Sigma Chemical Co., Poole, Dorset, England.

(e) Signal-Preventing Zone 75 mM sodium ascorbate in distilled water.

(f) Development of the Strip. Assay of Progesterone.

The following reagents were added to the strip;

(i) 50 $\mu$l of 75 mM sodium ascorbate in distilled water applied 4 cm from the bottom of the strip.

(ii) 50 $\mu$l of progesterone-HRP 1:20,000 dilution in phosphate-buffered saline containing 1% BSA applied 6 cm from the bottom of the strip.

(iii) 50 $\mu$l of solid-phase antibody reagent applied 9 cm from the bottom of the strip.

Three test samples were prepared by dissolving progesterone in phosphate buffered saline containing 0.1% BSA at 0, 5 and 10 ng ml$^{-1}$. Each test sample was applied to a test-strip at the enzyme-labelled reagent zone. Each strip was then developed the full length with developing solution (b). Ten minutes after the developing solution had reached the top of each strip, a blue colour was observed at the indicator reagent zone of the strips to which 0 and 5 ngml$^{-1}$ progesterone had been applied. However, no colour was observed at the indicator reagent zone of the strip to which 10 ng ml$^{-1}$ progesterone had been applied. Thus the assay could detect the presence of progesterone above 10 ng ml$^{-1}$.

The absence of colour indicated that at 10 ng ml$^{-1}$ the sample progesterone had successfully competed with the progesterone-HRP conjugate for the binding sites of the immobilised antibody, while at 5 ngml$^{-1}$ sufficient conjugate was permitted to bind to the antibody to subsequently react with $H_2O_2$ and TMB to generate the blue signal. As in Example 2, the presence of ascorbate prevented the generation of the blue signal throughout the strip except at the indicator reagent zone.

I claim:

1. A method of performing an enzyme-labeled binding assay comprising:

(a) adjoining an absorbant material with a reservoir containing a developing solution comprising a substrate of an enzyme of an enzyme-labeled reagent that acts upon said substrate to produce a detectable signal, or to produce a substrate which in turn is acted upon by a signal-producing enzyme reaaent to produce a detectable signal, said absorbant material being provided with a sample-receiving zone, a plurality of sequential and transverse reagent zones comprising immobilized or non-immobilized reagents, including an immobilized indicator reagent zone capable of directly or indirectly immobilizing said said enzyme-labeled reagent in an amount dependent on the assay result, and also including a reagent zone comprising an immobilized or non-immobilized reagent that prevents a signal formation except where the enzyme-labeled reagent is immobilized at the indicator reagent zone, wherein said reagent that prevents signal formation is in excess concentration relative to the concentration of the enzyme-labeled reagent and the substrate;

(b) applying a sample to be assayed to said sample receiving zone;

(c) applying the developing solution to said absorbing material so that as the developing solution advances through said absorbing material, the solvent front of said advancing developing solution proceeds sequentially through the reagent zones, and the non-immobilized reagents and the substrate co-migrate at the developing solution solvent front; and (d) allowing the solvent front to proceed through and past the immobilized indicator reagent zone so that the reagent that prevents signal formation is removed from the immobilized indicator reagent zone and a signal is formed, wherein said signal is dependent on the assay result.

2. The method according to claim 1 wherein the absorbent material is in the form of an elongate strip with transverse reagent zones.

3. The method according to claim 2 wherein the absorbent material bibulous paper.

4. The method according to claim 1 wherein the reagent that prevents signal formation is (1) a reversible inhibitor of the enzyme-labeled reagent; (2) a further enzyme or a reagent which will compete with the enzyme-labeled reagent for substrate or cofactors; (3) an alternative substrate for the enzyme-labeled reagent which is not chromogenic and competes with the signal-producing substrate for the enzyme; (4) an end-product of a reaction catalyzed by the enzyme-labeled reagent which is able to inhibit the enzyme; or (5) a reagent which is able to maintain the pH in the locality of the enzyme-labeled reagent away from the pH optimum of the enzyme.

5. The method according to claim 4 wherein the reagent that prevents signal formation is an enzyme or reagent which will compete with the enzyme-labeled reagent for substrate or cofactors.

6. The method according to claim 4 wherein the reagent that prevents signal formation is a reductase or a reducing agent and the enzyme-labeled reagent is an oxidoreductase-labeled reagent.

7. The method according to claim 6 wherein the oxidoreductase is a peroxidase.

8. The method according to claim 7 wherein the peroxidase is horseradish peroxidase.

9. The method according to claim 4 wherein the reagent that prevents signal formation is catalase.

10. The method according to claim 4 wherein the reagent that prevents signal formation is ascorbic acid or a salt thereof.

11. The method according to claim 10 wherein the reagent that prevents signal formation is sodium ascorbate.

12. The method according to claim 1 for determining the relative concentrations of two sample analytes.

13. The method according to claim 12 for determining the relative concentrations of pregnanediol-3-glucuronide and oestrone-3-glucuronide in urine.

14. The method according to claim 1, which is a competitive binding assay.

15. The method according to claim 14 wherein a sample analyte competes with the enzyme labeled reagent for binding to the immobilized indicator reagent zone.

16. The method according to claim 14 wherein an analyte in the sample binds to an enzyme labeled reagent or binds to a reagent in competition with an enzyme labeled analyte analogue.

17. The method according to claim 1, which is a non-competitive binding assay.

18. The method according to claim 1 wherein the signal produced in the indicator reagent zone is fluorometric, chemiluminometric or calorimetric.

* * * * *

UNITED STATES PATENT AND TRADEMARK OFFICE
CERTIFICATE OF CORRECTION

PATENT NO. : 5,861,265
DATED : January 19, 1999
INVENTOR(S) : PERRY

It is certified that error appears in the above-indentified patent and that said Letters Patent is hereby corrected as shown below:

On the title page, item [63], line 5, after "Feb. 22, 1989, abandoned", insert --which is a continuation of PCT/GB88/00329 filed Apr. 28, 1988--.

In claim 1 at column 18, line 64, replace "reaaent" with -- reagent --.

In claim 1 at column 19, line 4, delete the first occurrence of "said".

In the second line of claim 3 in column 19, insert -- is a -- after "material".

Signed and Sealed this

Seventeenth Day of August, 1999

*Attest:*

Q. TODD DICKINSON

*Attesting Officer*     *Acting Commissioner of Patents and Trademarks*